United States Patent
Childers et al.

(10) Patent No.: US 6,886,557 B2
(45) Date of Patent: May 3, 2005

(54) INHALATION DEVICE AND METHOD FOR DELIVERING VARIABLE AMOUNTS OF DIFFERENT COMPONENTS

(75) Inventors: Winthrop D. Childers, San Diego, CA (US); David Tyvoll, La Jolla, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 161 days.

(21) Appl. No.: 10/286,204

(22) Filed: Oct. 31, 2002

(65) Prior Publication Data

US 2004/0084044 A1 May 6, 2004

(51) Int. Cl.[7] ............................................. A61M 11/00
(52) U.S. Cl. ......................... 128/200.14; 128/200.19; 128/200.23; 128/203.12; 128/202.21
(58) Field of Search ................... 128/200.14, 200.19, 128/200.23, 203.12, 204.21, 204.23, 202.21; 131/273

(56) References Cited

U.S. PATENT DOCUMENTS

| | | | | |
|---|---|---|---|---|
| 4,554,916 A | * | 11/1985 | Watt ........................ | 128/203.12 |
| 4,657,008 A | * | 4/1987 | Broddner et al. ......... | 128/203.27 |
| 4,938,236 A | * | 7/1990 | Banerjee et al. .......... | 131/194 |
| 4,953,572 A | | 9/1990 | Rose et al. | |
| 5,067,500 A | * | 11/1991 | Keritsis ..................... | 131/335 |
| 5,284,133 A | | 2/1994 | Burns et al. | |
| 5,331,953 A | | 7/1994 | Andersson et al. | |
| 5,363,842 A | | 11/1994 | Mishelevich et al. | |
| 5,404,871 A | * | 4/1995 | Goodman et al. ......... | 128/200.14 |
| 5,642,731 A | | 7/1997 | Kehr | |
| 5,894,841 A | * | 4/1999 | Voges ....................... | 128/203.12 |
| 6,024,097 A | * | 2/2000 | Von Wielligh ............ | 131/270 |
| 6,202,642 B1 | * | 3/2001 | McKinnon et al. ....... | 128/200.23 |
| 6,234,167 B1 | | 5/2001 | Cox et al. | |
| 6,571,790 B1 | * | 6/2003 | Weinstein ................. | 128/200.19 |
| 6,684,880 B2 | * | 2/2004 | Trueba ..................... | 128/200.16 |
| 2002/0129812 A1 | * | 9/2002 | Litherland et al. ....... | 128/200.14 |

FOREIGN PATENT DOCUMENTS

| DE | 2346730 | 4/1975 |
|---|---|---|
| WO | WO0204055 | 1/2002 |

OTHER PUBLICATIONS

EP search report dated Feb. 2, 2004.

* cited by examiner

*Primary Examiner*—Henry Bennett
*Assistant Examiner*—Amanda Flynn (57) ABSTRACT

An inhalation device configured to programmably emit small droplets of multiple components in which quantities of the multiple components can vary with each successive activation of the inhalation device.

35 Claims, 4 Drawing Sheets

INHALATION DEVICE AND METHOD FOR DELIVERING VARIABLE AMOUNTS OF DIFFERENT COMPONENTS

BACKGROUND OF THE INVENTION

The present invention is directed to an inhalation device capable of delivering multiple materials in programmably varying amounts over time. The present invention is also directed to a method for administering programmably variable doses of multiple inhalable materials.

Inhalation devices provide a mechanism and device for pulmonary delivery of certain pharmacologically active materials. The use and effectiveness of such devices can be limited because the devices cannot be configured to prevent interactive overdose or to regulate the timing of the administration of doses of multiple pharmacologically active material in one device.

Medicinal formulation requirements can also make the use of inhalation devices for combinational therapy difficult. Certain medicinal compositions are most advantageously compounded in water-based solutions, others in alcohol-based compounds, while others can be dry administered. Currently inhalation devices can be configured to dispense a single carrier. Thus current inhalation devices administering current combinational therapies must employ drugs which are compatible with one another in a single carrier vehicle. This may limit potentially useful drug combinations.

Inhalation devices have found only limited application in programs or strategies which are designed to wean an individual from substances causing psychological or physical dependence; i.e., nicotine. Such devices could have significant efficacy in smoking cessation programs as the smoking cessation activity should address both the physical dependence on the addictive drug, i.e., nicotine; as well as sociological and psychological dependence typically associated with the method of delivery; i.e. inhalation. One difficulty encountered with prior smoking cessation devices and products is the tendency for the user to revert back to the original habit as the effect of the delivered nicotine ramps down. Additionally such products do not adequately address the psychosocial need of the user to repeatedly take a dose from a mouth activated device which, if not addressed, can lead to overdose or reversion to the original habit. Thus, a device which addresses the physical and psychosocial aspects of the behavior to be curbed or eliminated would be highly desirable.

SUMMARY OF THE INVENTION

Disclosed is an inhalation device and a method for delivering multiple inhalable materials in programmably varying amounts over time. The inhalation device includes an inhalation chamber and control electronics having an information storage portion. The inhalation device also includes first and second microfluidic aerosol generators whose function is governed by the control electronics. The first and second microfluidic aerosol generators are capable of emitting droplets of first and second materials, respectively, into the inhalation chamber. The information storage portion includes information pertaining to quantities of the first and second materials to be emitted with each activation of the inhalation device. The quantities of the first and second materials can vary with respect to each other.

DETAILED DESCRIPTION OF THE EMBODIMENT

Disclosed is an inhalation device which can programmably emit small droplets of multiple components for use in various inhalation therapy regimens. Such inhalation therapy regimens include, but are not limited to, the administration of active drugs and adjuvants as part of medical therapy programs for acute and/or chronic pulmonary diseases and conditions; the administration of materials capable of pulmonary uptake useful in the treatment of acute and/or chronic non-pulmonary conditions and diseases; and regimens and treatment programs designed to decrease or eliminate psychological and/or physiological dependence on compounds capable of pulmonary uptake or effect. Thus it is contemplated that the inhalation device as disclosed can be used in areas which include, but are not limited to, administration of various prescription and nonprescription drugs useful in pulmonary therapy and/or other therapies employing pulmonary uptake drugs and in various smoking cessation regimens.

Figure 1:
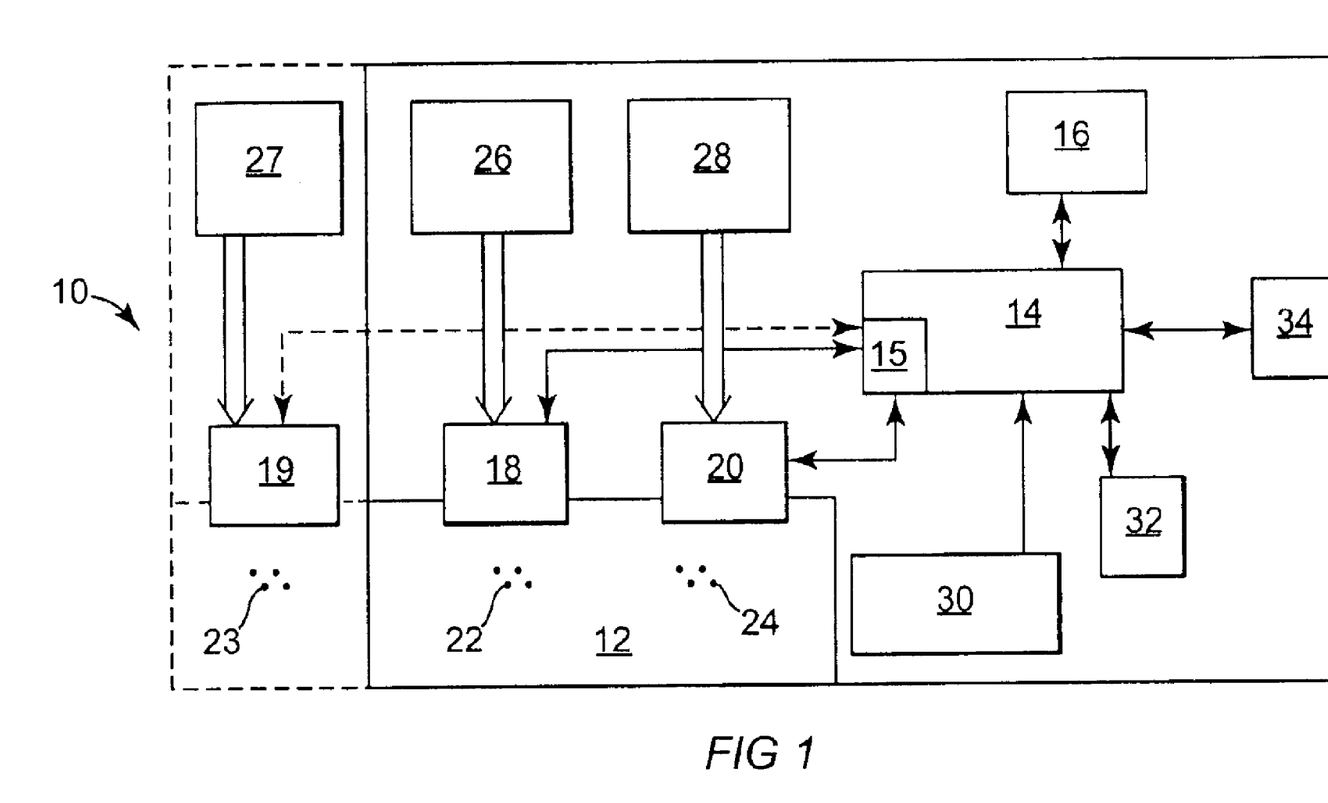
FIG. 1 is a schematic representation of an inhalation device according to an embodiment.

One embodiment schematically depicted in FIG. 1 is an inhalation device 10 which includes an inhalation chamber 12 and control electronics 14 which are associated with or include an information storage portion or memory 16. The inhalation device also includes first and second microfluidic aerosol generators 18, 20 capable of emitting or delivering droplets 22, 24 of first and second materials, respectively, into the inhalation chamber 12. One or more of the materials may be either be either pharmacologically active or inactive depending on factors which may include, but are not limited to, the nature of the inhalation regimen, the point in time in the given regimen at which the material is administered and the like. In the inhalation device 10 of the present invention, the information storage portion 16 is configured to contain and/or receive information governing the quantities of the first and second materials to be ejected with a given activation of the inhalation device 10. The quantities of the first and second materials can programmably vary relative to one another. Variation of quantities of materials can occur over time, at given intervals, or can occur after a desired number of activations of the inhalation device 10. It is contemplated that emitted quantities can vary from activation to activation or can remain constant for a defined number of activations or for a defined interval regardless of the number of activations depending upon various parameters such as the particular application or the nature and composition of materials administered.

The inhalation chamber 12 may be of any suitable configuration which will permit the introduction of the desired materials and facilitate their passage into the airway of the user. It is envisioned that the chamber may be defined as a passage surrounded by a suitable housing (not shown). In such configuration, it is envisioned that the housing can be adapted to be removably inserted into the mouth of the user in the manner of a straw or the like.

Control electronics 14 may be any configuration of hardware and/or software maintaining logic and circuitry capable of interactive function with the microfluidic aerosol generators 18, 20 employed in the inhalation device 10. As depicted in FIG. 1, it is contemplated that suitable control electronics 14 can be capable of interactive communication and control with associated microfluidic aerosol generators 18, 20 as well as receiving input from various other sources and devices which include, but are not limited to sensor 30, chronometric device 32 and user interface 34.

Information storage may occur in the information storage portion 16. Pertinent information includes, but is not limited to, data regarding dosing instructions, drug interactions, dosage interval and the like. It is contemplated that such information may be pre-programmed into the information storage portion prior to initial use or activation. However, it is also considered within the purview of this invention that the information storage portion 16 may be configured to receive command instructions at any point during the use and cycle of the inhalation device 10. Thus, in certain embodiments, it is contemplated that the information storage portion 16 may be configured to receive various operational instructions from a physician, pharmacist or the like. Such operation instructions may augment basic programming and dosing administration information.

It is also contemplated that the information storage portion 16 may be configured to receive information generated during the operation of the inhalation device 10. Such information can include, but is not limited to, use frequency, elapsed interval since last operation, amounts of various materials administered (dose trend and/or total dose) and the like. The information collected is that which would be relevant to calculation and control of subsequent quantities of material produced by microfluidic aerosol generators 18, 20.

It is envisioned that information contained in the inhalation device 10 will be that which is indicative of control parameters. The information may be contained in a manner or nature which is directly converted into appropriate control signals. Thus, the information stored need not be directly readable from the device.

The inhalation device 10 also includes first and second microfluidic aerosol generators 18, 20. While first and second microfluidic aerosol generators 18, 20 are specifically depicted and discussed, it is to be understood that the inhalation device 10 of the present invention may include any number of generators desired or required to introduce various materials into the inhalation chamber 12 and ultimately into the airway of the user. As described herein, a first generator may introduce or emit a pharmacologically active material. A second generator may introduce an associated material which may be pharmacologically active or inactive as desired or required. The present invention contemplates the use of multiple generators for introduction of various associated materials where multiple generators are required to facilitate introduction. In certain instances, it is contemplated that the aerosol generators may all be configured to emit materials which are strictly classified as pharmacologically inactive.

The first and second microfluidic aerosol generators 18, 20 may be suitable microfluidic devices capable of producing or emitting aerosolized of material in a size range and velocity which facilitates uptake and introduction into the airway of the user and eventual uptake of the pharmacologically active material in appropriate pulmonary tissue. Suitable microfluidic aerosol generators may incorporate control and structural features commonly associated with ink jet printing devices. Such devices can include, but are not limited to, piezoelectric devices, thermal fluid devices, and vibrating membrane devices with piezoelectric actuators capable of dispensing material in aerosol form upon receipt of an activation command.

The materials dispensed by microfluidic aerosol generators 18, 20 may be any type of fluidizable material which can be suitably dispensed or converted to aerosolized material. It is contemplated that liquids and fluidizable solids such as powders can be employed. "Aerosol" as used herein is taken to mean a gaseous suspension of liquid and/or solid particles.

The materials dispensed may be compounded or formulated into any suitable carrier material. The carrier material of choice will be one which is compatible with the particular active compound to be administered. Such carriers include, but are not limited to, gases and liquids suitable for human uptake and consumption. Liquids may include aqueous and/or organic materials. It is contemplated that various materials compounded or formulated in different carriers can be administered using the device 10 as disclosed where materials contained in different carriers are to be dispensed. The associated microfluidic aerosol generators 18, 20 can be suitably configured to accomplish effective administration of the various compositions. By way of non-limiting example, it is contemplated that physical characteristics of the firing chamber of the associated microfluidic device(s) can be configured to accommodate the different solvent/carrier media.

The first and second microfluidic aerosol generators 18, 20 may be fluidly coupled to any suitable source of respective pharmacologically active or inactive materials. As depicted in FIG. 1, suitable materials are maintained in suitable reservoirs 26, 28 in fluid communication with the associated microfluidic aerosol generators 18, 20. The representation of first and second microfluidic aerosol generators 18, 20 and associated reservoirs 26, 28 will be understood to represent multiple generators and reservoirs as required. For example, as shown in phantom in FIG. 1, in one embodiment, inhalation device 10 further comprises a third microfluidic aerosol generator 19 (for emitting droplets 23) and a third associated reservoir 27 for maintaining a third material in fluid communication with the third generator 19. It is also contemplated that reservoirs 26, 28 which are depicted in FIG. 1 as separate entities may be separate chambers in a single storage device.

The inhalation device 10 may also include a suitable actuator which initiates ejection of droplets according to a suitable programmably variable regimen. The actuator may be a suitable trigger operated by the user to initiate dose dispensation or may be coupled with a suitable sensor or the like. As depicted in FIG. 1, a sensor 30 is in electronic communication with the control electronics 14 such that the occurrence of an externally originated event will trigger the emission of a signal from the sensor 30 to be received and 
interpreted by the control electronics 14. The externally originated event may be any of a number of occurrences which are of interest or relevant to the operation of the device. By way of nonlimiting example, the sensor 30 may be one which is capable of detecting changes in air flow through the inhalation chamber 12 associated with the intake of air by the user. Such an externally originated event detected by the sensor 30 could trigger the activation of the generators 18, 20 by the suitable control electronics 14. It is also possible that the sensor 30 can be one which registers the intensity of such an inhalation event and permits adjustment of the operation of the microfluidic aerosol generators 18, 20 accordingly. As seen in FIG. 1, a sensor 30 is positioned proximate to the inhalation chamber 12. Initiation of the inhalation event as detected by the sensor is translated into a signal transmitted to the control electronics 14 which, interactively with the information storage portion 16, generates a suitable firing command which is translated to the microfluidic aerosol generators 18, 20 to dispense appropriate quantities of the associated materials.

Figure 2A:
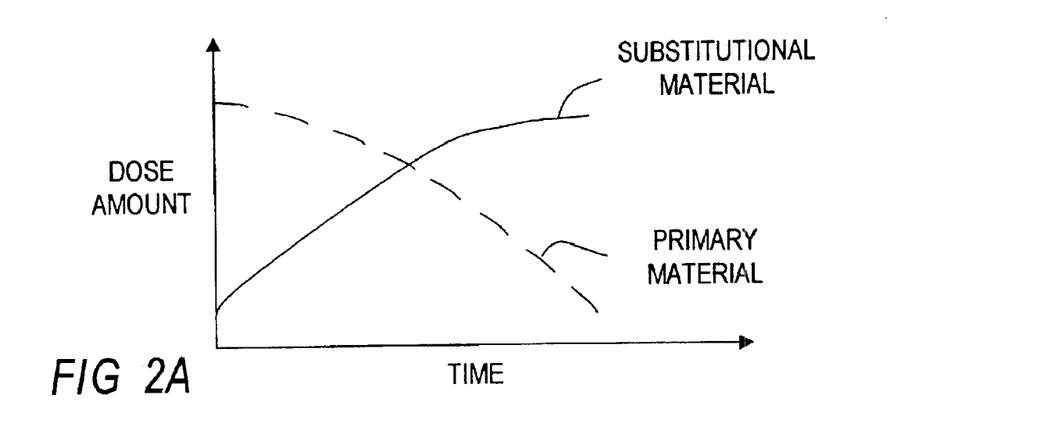
FIG. 2A is a representative qualitative plot of components delivered over time from an inhalation device according to an embodiment.

The inhalation device 10 may include other sensor(s) as desired or required to determine volume of material in associated reservoir(s) 26, 28, etc. Thus while inhalation sensors have been described, it is also contemplated that device 10 may include sensor(s) capable of detecting any other appropriate externally originated events. Thus, a sensor may be a touch sensor which permits on/off functioning of the inhalation device or any associated emitter or emitters as desired or required.

The inhalation device 10 may also include a suitable clock or chronometer 32 in interactive communication with the control electronics 14 to ascertain and measure values such as actual time, use interval, and use frequency. The chronometer or clock 32 can facilitate tracking of the administration of the administered material(s) so that proper administration versus time is attained and maintained.

In certain applications, the inhalation device 10 may be equipped with an interface 34 in electronic communication with the control electronics 14 and associated information storage portion 16. The interface 34 may permit the user or the user's physician or pharmacist to determine or set particular dosing or administration parameters.

The term "pharmacologically active material" is used herein to define materials which have a physiological and/or psychological effect on the user upon inhalation and/or pulmonary uptake. Pharmacologically active materials can include various regulated or controlled prescription drugs, as well as other nonprescription compositions or compounds including, but not limited to, nutraceuticals, and the like.

Physiological effect may include, but is not limited to, any of a number of known effects which occur in the human body rapidly or over time after uptake of the compound or composition. Non-limiting examples of such effects include changes to respiration rate or efficiency, changes in heart rate, blood pressure, temperature regulation and the like. Nonlimiting examples can also include changes in neurotransmitter function or uptake and the like. It is also contemplated that physiological effect may include complex but subtle interactions of various physical functions such as those enumerated. Materials having antibiotic or immunological activity are also considered within the purview of this disclosure.

The method and device as disclosed also contemplates the administration of materials which are considered pharmacologically inactive. Such materials include compounds for which the pharmacological effect is not currently known, proven or demonstrated. Such materials are traditionally considered placebos or palliative in nature. Such materials may not have a direct or measurable physical effect upon administration but will provide the user with a measure of satiation or satisfaction upon receipt.

The inhalation device 10 of the present invention may be configured such that an ejector such as first microfluidic aerosol generator 18 ejects a first material having primary pharmacological activity, i.e., a known or desired physical effect. An additional microfluidic aerosol generator such as generator 20 ejects a second material having secondary pharmacological activity. The term "secondary pharmacological activity" as used herein is defined as materials which, when administered, will elicit or will be perceived by the user to elicit a physical dose response which is complimentary to the physiological response elicited by the material having primary pharmacological activity. The second material may provide a suitable or compatible dose response or may have a palliative or placebo effect whereby the user is either distracted or palliated by the administration of the second material.

In one such non-limiting example of this, the first material having primary pharmacological effect is a material such as nicotine. The second material having secondary pharmacological activity can be any of a number of materials which will provide the user with some satisfaction upon administration. Thus where the first material is nicotine, the second material can be a compound or composition having a complimentary effect upon administration, i.e. caffeine, or a material having a palliative or distracting effect, i.e. a flavoring agent such as menthol. The second material is one which is noticeable upon administration and which can be held constant or increased as the amount of the first pharmacologically active material is decreased. Thus, the user is provided with a measure of satisfaction even when output of the first or primary material is reduced. The satisfaction may be due to a perception of receiving some material as a result of the inhalation event. It is also contemplated that administration of complimentary materials having secondary pharmacological activity can contribute to a palliative effect which can provide short term distraction/satisfaction as the user proceeds with a weaning regimen.

The preprogrammed amount of a material having primary pharmacological activity can be decreased or altered in response to any number of factors which include but are not limited to elapsed time, use frequency, and a preprogrammed protocol. Thus, the control electronics of the inhalation device 10 of the present embodiment can include appropriate logic to alter the amount of the material having primary pharmacological activity in response to various inputs. For example, the amount of a material having primary pharmacological activity administered can be designed to decrease gradually over intervals of weeks or months to implement a suitable weaning protocol. The amount of material having primary pharmacological activity can also be temporarily decreased in response to increased use frequency or demand to maintain the weaning protocol.

It is also contemplated that the control electronics 14 and associated information storage component 16 may include appropriate logic to administer the material having primary pharmacological activity over a series of suitable dosage intervals. Thus the material may be administered in one inhalation event or a given dose may be administered over several inhalation events within a given interval. The interval governed by control electronics 14 can be configured to facilitate uptake of the material in therapeutic applications or could be configured to mimic the uptake interval for a material such as nicotine typically associated with smoking.

The control electronics 14 will also govern the amount of material having secondary pharmacological activity delivered contemporaneously with the primary material. The amount delivered will generally be one which is complimentary to the amount of primary material delivered. "Complimentary amount" is defined as an electronically programmable and variable amount of secondary material delivered which will either enhance activity and/or effect of the primary material administered or provide the user with a feeling or perception that the overall dosage of the primary material is the same or greater than prior doses despite actual decreasing amounts of the primary material or, at minimum, provide the user with a limited degree of satisfaction. To achieve this, the first and second components can be administered or emitted in a manner independent of one another in a continuously changing ratio depending upon any of a number of operational parameters. In FIG. 2, an exemplary dose curve for a two-component administration system is depicted in which the amount of the material having primary pharmacological activity is decreased over a given time interval. The time interval may be any suitable period such as days, weeks, or months depending upon the material administered. The decrease in quantity of the material having primary pharmacological activity is accompanied by a concomitant increase in the quantity of the second material having secondary or substitutional pharmacological activity. It is also contemplated that a weaning regimen can be implemented where the material having primary pharmacological activity is decreased while the amount of any secondary materials is maintained essentially constant. Such regimens would facilitate decrease in amounts of primary material administered in situations where such volume reductions are desired.

The material having secondary substitutional pharmacological activity can be a material or materials having an alternate pharmaceutical activity or can be a material or materials having a psychological or placebo effect. Such materials can be used alone or in suitable admixture.

In one embodiment, the inhalation device 10 can be utilized as a smoking cessation device to wean an individual from physical dependence on nicotine. In such situations the device 10 will include as a material having primary pharmacological activity such as a composition containing nicotine. The nicotine-containing material can be any formulation capable of pulmonary uptake and being dispensed in aerosol form. The term "nicotine-containing material" is employed herein to include compositions which contain nicotine or nicotine analogues which induce psychopharmacological dependence in the user.

Where the inhalation device 10 is employed as a smoking cessation device in a smoking cessation regimen, the device will contain at least one material having secondary or substitutional pharmacological activity. Such material may be a nicotine analog having an acceptable side effects panel. The material may be either synthetic or naturally occurring and can include at least one of flavoring agents or compounds, fragrance compounds, bronchodilators, adjuvants, and complimentary medicants. Examples of flavoring compounds include, but are not limited to eucalyptus extract, mint, mint oil, menthol, vanilla, and cocoa. Various materials function as bronchodilators which encourage expansion of airways and facilitate nicotine intake. Various adjuvants which can be successfully employed in combination with materials such as nicotine which have primary pharmacological activity include various adjuvants which can enhance the uptake or physiological effectiveness of materials such as nicotine. Nonlimiting examples of such adjuvants include ammonium compounds and materials such as levulinic acid.

It is also contemplated that the secondary substitutional pharmacological active material can include compounds which function as cough suppressants, expectorants and/or throat soothers. It is to be understood that the inhalation device 10 as disclosed can be configured to emit any number of primary and secondary substitutional pharmacologically active materials according to any logic or protocol.

The amount of various materials dispersed with a given activation of the inhalation device 10 of the present invention is governed by a control device such as control electronics 14. The information storage portion 16 of control electronics 14 can contain information that is indicative of control parameters and can be directly converted into control signals. Such control parameters can include a look-up table of possible control responses which converts into control signals which can result in variation in quantities of materials to be ejected based on parameters such as number and/or frequency of activations and the like.

It is also contemplated that the information storage portion 16 of control electronic 14 may include information based on a suitable mathematical algorithm(s) which serves to determine quantities of the various materials to be ejected with a given activation of the inhalation device 10. In this manner, the quantities can be varied with each successive activation according to any of a variety of input parameters.

The inhalation device 10 may include an appropriate lock-out mechanism 15 or electronic architecture to prevent inappropriate emission of a pharmacologically active material or materials. The lock-out mechanism 15 and/or architecture can be configured to prevent emission greater than the maximum threshold dose at a given interval or intervals. It is also contemplated that suitable lock-out mechanism 15 and/or architecture could be employed to prevent disabling of or tampering with the inhalation device.

When the inhalation device 10 of the present invention is employed as a smoking cessation device, it is contemplated that the control electronics 14 will be calibrated to deliver decreasing quantities of nicotine-containing material over time until the user's psychopharmacological dependence on the material has abated. Thus, on a macro-dosage administration level, it is contemplated that the volume of nicotine-containing material administered and the volume of an associated smoking cessation agent administered can follow a dose curve similar to that depicted in FIG. 2A. In such administration strategy, the amount of the associated smoking cessation agent is ramped up to offset perceived decrease in the nicotine dosage and to provide the user with a degree of satisfaction or palliation. It is contemplated that the control electronics 14 will operate to programmably decrease nicotine administered per administration interval over time. Typically, the total daily dose of nicotine delivered will programmably decrease over a treatment interval measured in weeks or months. However, it is understood that the treatment interval can be varied depending upon factors such as the needs of the user or the rapidity with which the decrease is desired.

Figure 2B:
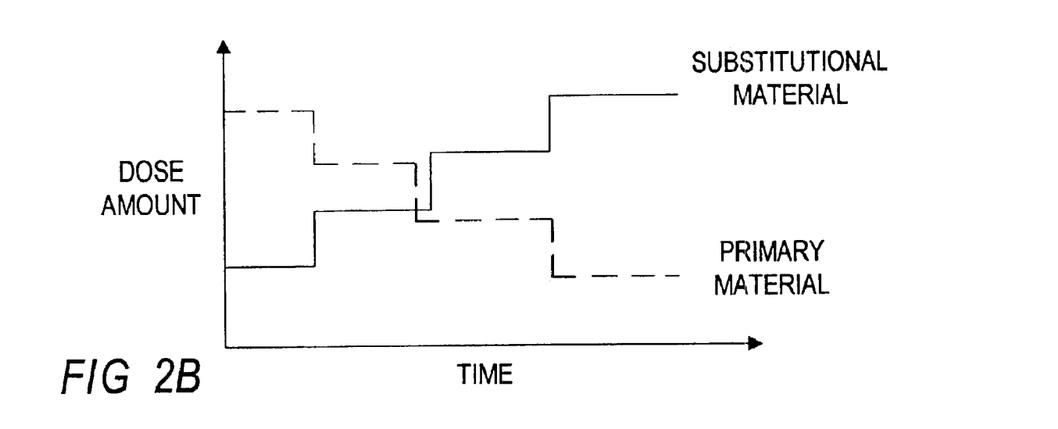
FIG. 2B is a representative qualitative plot of components delivered over time.
Figure 3:
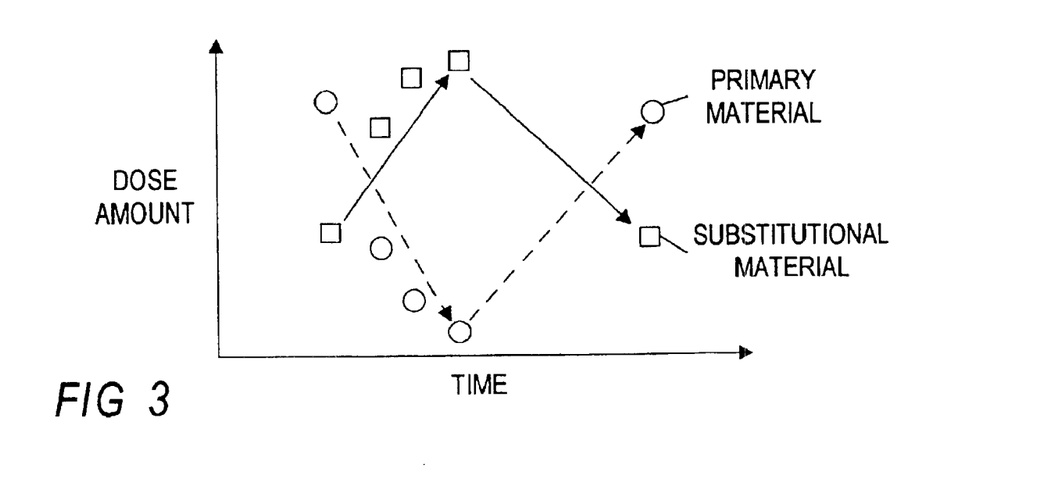
FIG. 3 is a representative qualitative plot of multiple doses of two components delivered from an inhalation device according to an embodiment.

It is also contemplated that dosage administration can ramp down in a plurality of staged similar or identical dosage administrations. One such exemplary scenario is depicted in FIG. 2B which plots administration of a material having primary pharmacological activity such as nicotine over multiple inhalations at a given dose. In this way the user can receive a constant dose of nicotine per inhalation for an interval of days or months as desired or required with staged step down in dosage at defined intervals.

Figure 4A:
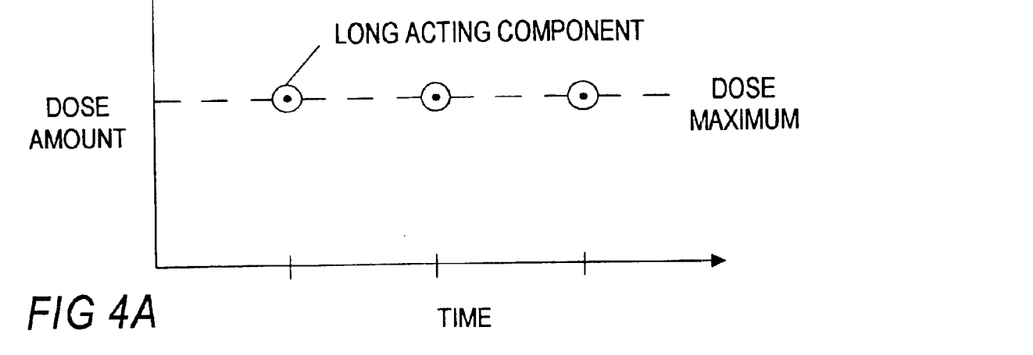
FIG. 4A is a graphic representation of one component of a three-component system administered over time from the inhalation device according to an embodiment.
Figure 4B:
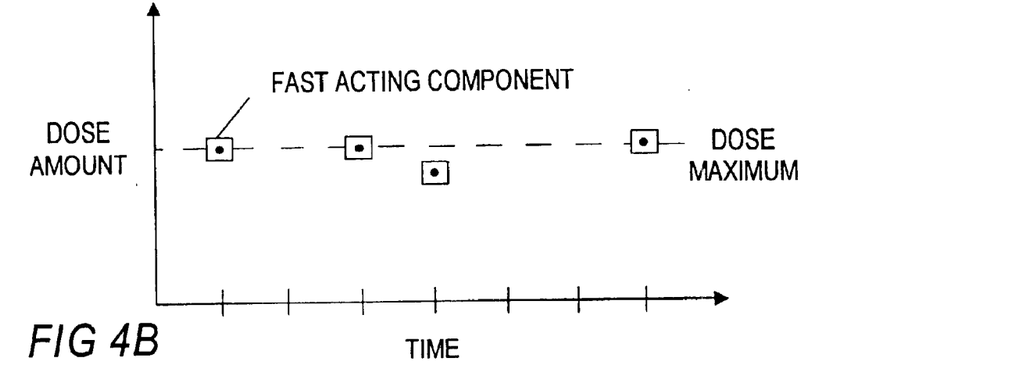
FIG. 4B is a graphic representation of a second component of a three-component system administered over time from the inhalation device according to an embodiment.

The control electronics 14 in combination with the microfluidic aerosol generators 18, 20 can provide for the independent and continuously changing administration curves for at least two different components from a single device 10 where desired or required. When the device 10 is employed as a smoking cessation device, it is contemplated that an aerosol generator such as generator 18 can dispense a nicotine-containing fluid material from reservoir 26. The amount or volume of nicotine-containing material present in reservoir 26 can be an amount sufficient to implement the smoking cessation regimen. Alternately, it is contemplated that device 10 can be configured such that various reservoirs and/or associated aerosol generators can be removed and replaced as necessary.

When the inhalation device 10 as disclosed is employed as a smoking cessation device, it is contemplated that reservoir 28 will contain a suitable smoking cessation agent, for example, one of the materials or compounds enumerated previously. It is also contemplated that the device 10 can include multiple reservoirs or chambers containing various smoking cessation compounds which can be dispensed simultaneously or in sequence in any suitable combination from microfluidic aerosol generator 20 or additional generators (not shown). Suitable combinations and quantities of the various smoking cessation agents can be governed by the control electronics 14 and associated logic and control procedures as could be contained in the information storage portion 16.

In the smoking cessation regimen, it is contemplated that microfluidic aerosol generators 18 and 20 will activate contemporaneously to deliver a mixture of the two associated components into inhalation chamber 12 where they are drawn into the airway of the user with associated air intake.

The control electronics 14 can be configured to provide administration of the nicotine-containing material in any suitable manner or dose pattern. Thus, a single dose of nicotine may be administered with a single inhalation event if desired or required. Alternately, the desired dose of nicotine-containing material may be metered over multiple rapid inhalation events to mimic the experience a user would have in receiving nicotine through a conventional cigar or cigarette.

As indicated by the graphs depicted in FIG. 2A and FIG. 2B, it may be desirable for the dosage of the smoking cessation agent 38 to increase over time as the dosage of nicotine-containing material 36 is decreased. While the graphs depicted in FIG. 2A and FIG. 2B are simplifications of this pattern, it is contemplated that there may be usage patterns of the device which will result in different administration patterns of the usage or intake of primary nicotine-containing material with respect to the substitutional smoking cessation material.

It is also contemplated that short term adaptations in dose administration can be implemented. In such situations the user may, in a given circumstance, want to suddenly receive very frequent dosages from the inhalation device 10. In order to provide the planned amount or dosage of nicotine, the device will decrease or eliminate nicotine output as the prescribed daily or hourly dosage is approached. In that case, the dosage pattern over the short term will not follow a smooth continuous curve as depicted qualitatively for long term administration in the graph in FIG. 2A or the stepped administration pattern as depicted in FIG. 2B. As depicted in FIG. 3, the user receives the normal dosage of nicotine-containing material initially. This is quickly followed by attempting to take two more administrations. The device initially provides a full dose of nicotine, but responds to the additional quick demands by sharply curtailing or shutting off the amount of nicotine-containing material delivered; keeping the total hourly or daily dosage in an acceptable range. To provide the user with a feeling of some degree of satisfaction or palliation, the amount of the associated substitutional material, i.e. smoking cessation agent, is rapidly increased to offset the decrease in nicotine-containing material. Thus, volumetrically and psychologically, the user has the perception of receiving an inhaled dose. After a prescribed amount of time, such as the normal time between doses, the user can then receive an additional dose of nicotine-containing material according to the associated smoking cessation program.

The variation between nicotine-containing material and associated smoking cessation agents ejected is governed by the control electronics 14. The control electronics 14 can include logic to vary the quantities of nicotine-containing material and the associated smoking cessation agent administered in response to at least one factor such as the programmed dispensing regimen, elapsed time and use frequency.

Where the inhalation device 10 as disclosed is employed as a smoking cessation device, it is contemplated that the smoking cessation agent can be a material or combination of various materials which will function to satiate or minimize the user's need for nicotine between prescribed doses. Such smoking cessation agents can include at least one of flavoring compounds, fragrance compounds, bronchodilators, adjuvants and complimentary medicants such as those previously enumerated. It is to be understood that the smoking cessation agent can be a composition which includes one or more of the aforementioned materials.

The inhalation device 10 as disclosed can be used as a smoking cessation device to administer nicotine and smoking cessation agents according to a variety of administration regimens. Thus, it is contemplated that the system can be configured to ramp up smoking cessation agent delivery with ramp down in delivery of nicotine-containing material. Alternately, the device can be configured to deliver a relatively constant dose of smoking cessation agent while the amount of nicotine-containing material is decreased.

Inhalation device 10 of the present invention can also be employed in long-term or short-term medical treatment regimens which require the administration of multiple long-acting and short-acting drugs which are susceptible to pulmonary absorption. By way of hypothetical example, FIGS. 4A and B illustrate the administration pattern for components A and B, a long-acting asthma drug and a short-acting asthma drug. Component A may have an ideal regimen such as graphically depicted in FIG. 4A in which material is ideally inhaled every twelve hours. A nonlimiting example of such material would be ipotropium bromide.

In asthma treatment regimens, it is also contemplated that various short-acting asthma drugs may be necessary to provide fast treatment for acute symptoms. The graphic representation depicted in FIG. 4B illustrates a hypothetical administration pattern for a rapid-acting component B of which albuterol sulfate is a nonlimiting example. Materials such as albuterol sulfate are intended for quick relief of acute symptoms. If taken more than a certain number of hours apart, a full dose of component B is appropriate. However, if taken twice over a very short interval, reduced doses of component B are required to prevent overdosing. In the inhalation device 10 of the present invention, the quantity of component B emitted from an associated aerosol generator is reduced to prevent overdosing as indicated in FIG. 4B. Dosage reduction can also be controlled and executed to address and avoid inappropriate drug interactions as may occur when multiple drugs interact synergistically to provide an enhanced effect. It is contemplated that dosage reduction and control is accomplished by the control electronics 14 and associated logic and programming in the storage portion 16.

In various medical treatment regimens, it is also possible to include a third component having a limited effect or even a placebo effect. By "limited or placebo effect," it is contemplated that the action of component C may be one which is considered non-prescription but may have certain psychological or palliative action. Such materials may include nutraceuticals and/or nonprescription compounds.

Figure 4C:
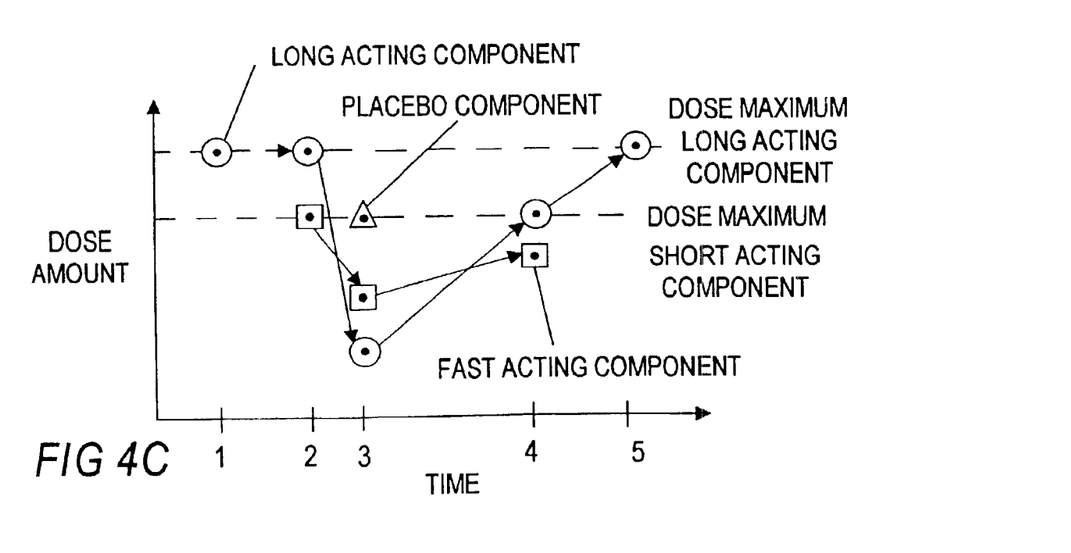
FIG. 4C is a graphic representation of three components administered over time from the inhalation device according to an embodiment.
Figure 5:
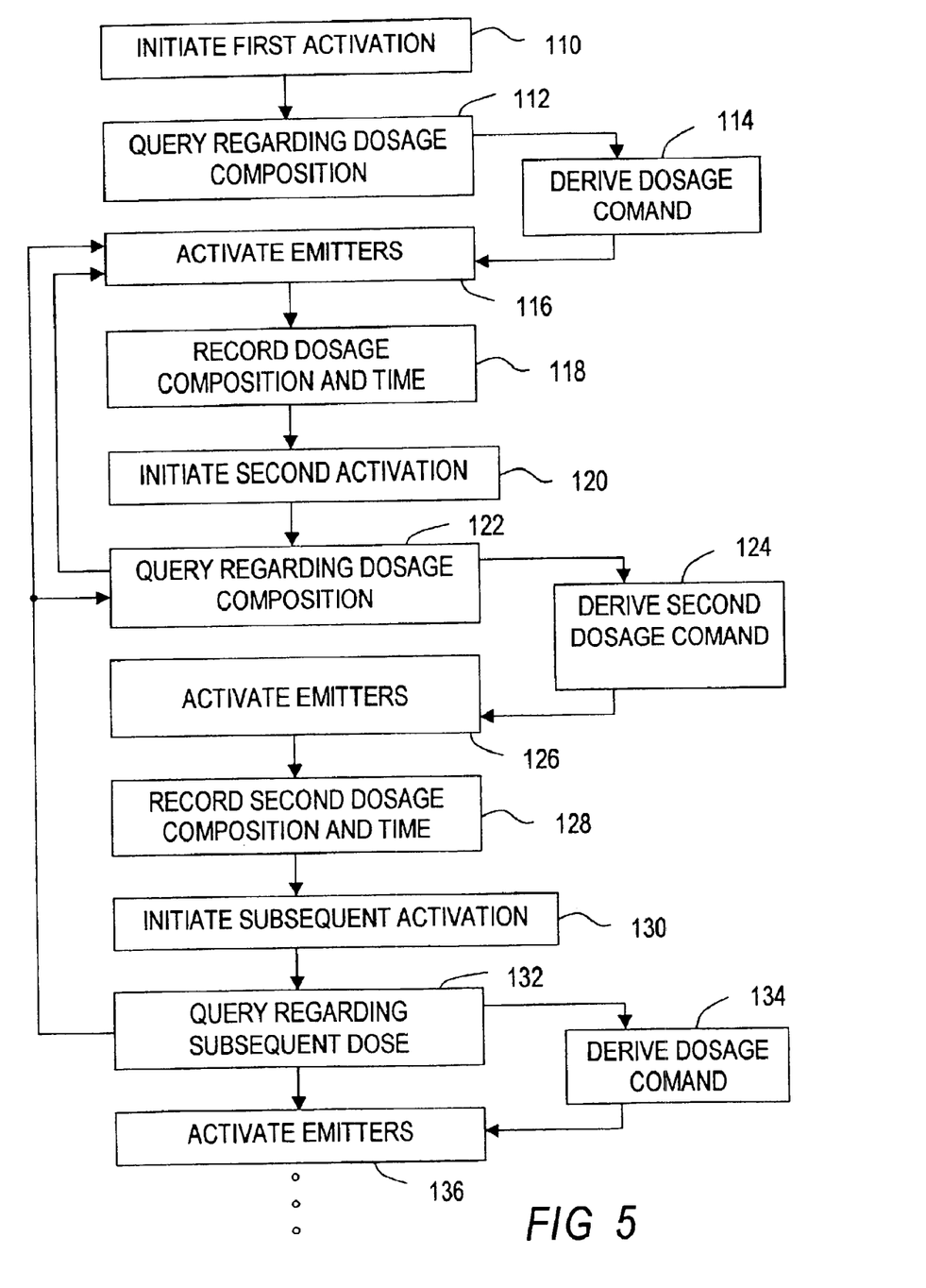
FIG. 5 is a process diagram of the sequence of operation of the inhalation device and method according to an embodiment.

One such administration regimen is graphically depicted in FIG. 4C. The inhalation device provides two options: The administration regimen for compound A is maintained and permitted. Additionally the user may opt for an additional short term dosing for acute symptoms as indicated by the addition of component B. As illustrated in FIG. 4C, the exemplary administration depicts a user taking doses at various times as indicated by non-uniform intervals 1, 2, 3, 4 and 5.

Initially, the user receives the default dose for the long-acting drug, component A. In the hypothetical progression set forth in FIG. 4C, when the time comes for the next administration of component A at interval 2, the user is experiencing bronchial difficulty and elects to take component B as well. Because components A and B are appropriate for contemporaneous administration and component B has not been taken recently, the user receives a full dose of both components A and B. Alternately, where materials are not appropriate for full dose administration, the amount of one component taken may be reduced when a second component is administered. Such dosage adjustment and reduction would be governed by information contained in the control electronics 14 and associated memory portion 16.

In the hypothetical dose sequence set forth in FIG. 4C, the user is still experiencing symptoms at interval 3. However, the elapsed time since prior dosage is sufficiently short that a full dose of component A or component B could cause a systemic overdose. Thus, the control electronics 14 provides for operation of the associated microfluidic aerosol generators 18, 20 in a manner such that the quantities of long-acting component A and component B are reduced to acceptable levels. As depicted in FIG. 4C, the inhalation device also provides for dispensing of component C, a placebo or another active component, to provide quick relief of symptoms. The inhalation device 10 can also be calibrated to provide small quantities of component A where it is determined that a small but steady input of component A is better than larger doses given certain circumstances or where it may be possible that the user has forgotten the next regularly scheduled dosage of component A.

At Interval 4, the user is still experiencing pulmonary symptoms. Administration of component B is permitted. At this point, the interval since the last dose of component B is long enough to permit full dosage of component B. However, the quantity of component A administered is reduced to an intermediate dosage based upon data contained in the lookup table or calculated from suitable control algorithms. Interval 5 is included to demonstrate an interval at which the user no longer experiences symptoms and receives the regular regimen dose of component A.

Thus, the present invention is directed to an inhalation therapy method which comprises the steps of delivering a first dose of an inhalable composition programmably emitted from a microfluidic aerosol generator into the airway of a user. The first dose of the inhalable composition comprises initial quantities of first and second pharmacologically active materials. The inhalation therapy method further includes a step in which a second dose of inhalable composition is delivered into the airway of a user after being programmably emitted from the microfluidic pump device. The second dose of inhalable composition comprises second quantities of the first and second pharmacologically active materials in which at least one component of the second dose can vary from the respective initial quantity. The quantities of the first and second materials are programmably emitted by the microfluidic aerosol generator as governed by information contained in suitable control electronics associated with the generator. Similarly, the present invention also contemplates a smoking cessation method which includes the steps of delivering a first dose of an inhalable composition into the airway of a user in which the inhalable composition comprises an initial quantity of nicotine-containing material and an initial quantity of a smoking cessation agent. The nicotine-containing material and the smoking cessation agent are emitted from a microfluidic aerosol generator. In the smoking cessation method of the present invention, a second dose of inhalable composition is delivered into the airway of the user and is emitted from a microfluidic aerosol generator. The second dose comprises an amount of the nicotine-containing compound and an amount of the smoking cessation material in which at least one of the nicotine-containing compound(s) and the smoking cessation agent(s) varies from the respective initial quantity emitted. In the smoking cessation method, the quantities of the nicotine-containing compound(s) and the smoking cessation agent(s) emitted from the microfluidic aerosol generator are governed by information contained in suitable control electronics associated with the microfluidic aerosol generator.

Basic operation sequence is depicted at FIG. 5 in which a first activation of the device is initiated 110 and prompts the query of the control electronics at 112 regarding the initial dose to be dispensed. A dosage command is derived at 114 from control electronics and data contained in storage portion at which results in a signal to activate emitters 116 causing the emission of the quantity of materials designated. The dose composition and time of dose administration is recorded at 118 for future reference and review. A second activation is initiated at 120 which prompts a query regarding composition of the second dose at 122. The query regarding second dose composition includes analysis of information regarding dosage as well as integration of information recorded regarding initial dose composition and time stored in the appropriate memory portion of the control electronics. When the appropriate dose is determined at 124, the generators are activated at 126 and the second dose composition and time is recorded at 128. Subsequent activations can be initiated as indicated at 130 with suitable queries 132 of the stored information including previous records of dose composition and the timing of various dose administrations. A subsequent dosage command can be derived at 134 and generators can be activated at 136. Thus, dosages can be programmably emitted and varied based upon appropriate protocol, use frequency, and elapsed time.

While the invention has been described in connection with what is presently considered to be the most practical and preferred embodiment, it is to be understood that the invention is not limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as permitted under the law.

What is claimed is:

1. An inhalation device comprising:

an inhalation chamber;

control electronics having an information storage portion;
   first and second microfluidic aerosol generators governed by the control electronics, the first and second microfluidic aerosol generators capable of contemporaneously emitting droplets of a first material and a second material, respectively, into the inhalation chamber to form a single inhalable composition, wherein the first and second materials are pharmacologically different from each other;

a reservoir in fluid communication with the first and second microfluidic aerosol generators and including a plurality of chambers with a first chamber and a second chamber in fluid communication, respectively, with the first and second aerosol generators, the first chamber configured to contain the first material and the second chamber configured to contain the second material;

wherein the information storage portion stores a regimen of doses to enable the control electronics to direct quantities of the first and second materials to be emitted with each activation of the inhalation device as the single inhalable composition, and to direct the quantities of the first and second pharmacologically different materials to vary with respect to each other to alter the concentration of the first material relative to the second material in the single inhalable composition over the regimen of doses.

2. The inhalation device of claim 1 wherein both the first and second materials are pharmacologically active.

3. The inhalation device of claim 2 wherein the first material has primary pharmacological activity and a second pharmacologically active material has substitutional pharmacological activity.

4. The inhalation device of claim 3 wherein the amount of the material having primary pharmacological activity is decreased in response to at least one of elapsed time, use frequency and a programmed weaning protocol, and wherein the amount of the material having substitutional activity is delivered in an amount complimentary to the amount of the material having primary pharmacological activity delivered.

5. The inhalation device of claim 4 wherein the material having primary pharmacological activity is nicotine.

6. The inhalation device of claim 5 wherein the material having substitutional pharmacological activity includes at least one of flavoring compounds, fragrance compounds, bronchodilators, adjuvants, and complimentary medicants.

7. The inhalation device of claim 6 wherein the flavoring compound includes at least one of eucalyptus extract, mint, mint oil and menthol.

8. The inhalation device of claim 6 wherein the flavoring compound includes at least one of vanilla and cocoa.

9. The inhalation device of claim 6 wherein the adjuvant compound includes at least one of ammonium compounds and levulinic acid.

10. The inhalation device of claim 6 wherein the complimentary medicant includes at least one of cough suppressants, expectorants, and throat soothers.

11. The inhalation device of claim 1 wherein the regimen of doses for quantities of the first and second materials to be emitted includes at least one of total dosage, programmed dispersing regimen, amounts of respective quantities dispensed, interval since last dispensation, and use frequency.

12. The inhalation device of claim 1 wherein the information storage portion of the control electronics includes a look-up table specifying quantities of the first and second materials to be ejected with each activation of the inhalation device.

13. The inhalation device of claim 1 wherein the information storage portion of the control electronics includes a mathematical algorithm controlling quantities of the first and second materials to be ejected with each activation of the inhalation device wherein quantities vary with each successive activation.

14. The inhalation device of claim 1 wherein the first and second microfluidic aerosol generators are microfluidic drop ejection devices, each microfluidic drop ejector configured to dispense an associated pharmacologically active material.

15. The inhalation device of claim 1 further comprising a sensor capable of detecting at least one externally originated event actionable on the device, the sensor capable of emitting at least one signal receivable by the control electronics.

16. The inhalation device of claim 1 wherein at least one of the first and second material is a fluidizable solid.

17. A smoking cessation device comprising:

an inhalation passage;

control electronics having an information storage portion;

first and second microfluidic aerosol generators under control of the control electronics, a first microfluidic aerosol generator delivering quantities of a nicotine-containing material and a second microfluidic aerosol generator delivering quantities of an associated smoking cessation agent contemporaneously with the nicotine-containing material, respectively, into the inhalation passage to form a single inhalable composition; a reservoir in fluid communication with the first and second microfluidic aerosol generators and including a plurality of chambers with a first chamber and a second chamber in fluid communication, respectively, with the first and second aerosol generators, and the first chamber configured to contain the nicotine-containing material and the second chamber configured to contain the associated smoking cessation agent including at least one of flavouring compounds, fragrance compounds, bronchodilators, adjuvants, and complimentary medicants;

wherein the information storage portion stores a regimen of doses to enable the control electronics to direct quantities of the nicotine-containing material and the associated smoking cessation agent to be delivered on each-activation of the smoking cessation device as the single inhalable composition, causing the quantity of the nicotine-containing material to decrease over the regimen and the quantity of the associated smoking cessation agent to increase over the regimen to alter the concentration of the nicotine-containing material relative to the associated smoking cessation agent in the single inhalable composition over the regimen of doses.

18. The smoking cessation device of claim 17 wherein the control electronics includes logic to regulate and vary quantities of nicotine-containing material and the associated smoking cessation agent in response to at least one of total dosage, programmed dispensing regimen, amounts of respective quantities dispensed, interval since last dispensation, and usage frequency.

19. The smoking cessation device of claim 17 further comprising at least one sensor capable of detecting at least one externally originated event actionable on the device, the sensor capable of emitting at least one signal receivable by the control electronics.

20. The smoking cessation device of claim 17 wherein the first and second microfluidic aerosol generators are microfluidic drop ejection devices.

21. The smoking cessation device of claim 17 wherein the associated smoking cessation agent includes at least one of flavoring compounds, fragrance compounds, bronchodilators, adjuvants, and complimentary medicants.

22. The smoking cessation device of claim 17 wherein the information storage portion of the control electronics includes at least one of a look-up table and an algorithm.

23. The smoking cessation device of claim 17 wherein the control electronics operate on the first and second microfluidic aerosol generators to administer total dose of nicotine-containing material over a defined interval and a variable amount of associated smoking cessation agent, the amount of associated smoking cessation agent administered determined by at least one of the amount of nicotine-containing material delivered, interval since last device activation, and frequency of activation.

24. The smoking cessation device of claim 17 further comprising a lockout mechanism for preventing emission of amount of nicotine in excess of a predetermined amount contained in the information storage portion.

25. The smoking cessation device of claim 17 further comprising a user interface device for permitting adjustment of the amount of smoking cessation agent delivered.

26. The smoking cessation device of claim 17 wherein delivered quantities of nicotine-containing material and quantities of associated smoking cessation agent vary with respect to number and sequence of activations of the inhalation device.

27. The smoking cessation device of claim 26 wherein delivered quantities of nicotine-containing material and quantities of associated smoking cessation agent remain constant over multiple activations.

28. The smoking cessation device of claim 26 wherein delivered quantities of nicotine-containing material and quantities of associated smoking cessation agent remain constant over a chronological interval.

29. An inhalation device comprising:

an inhalation chamber;

control electronics having an information storage portion and a chronometer;

first, second and third microfluidic aerosol generators under the control of the control electronics, the first, second, and third aerosol generators are capable of contemporaneously emitting droplets of first, second and third materials, respectively, into the inhalation chamber to form a single inhalable composition, wherein the first, second, and third materials are pharmacologically different from each other;

a reservoir in fluid communication with the first, second, and third microfluidic aerosol generators and including a plurality of chambers with a first chamber, a second chamber, and a third chamber in fluid communication, respectively, with the first, second, and third respective aerosol generators, wherein the first chamber is configured to contain the first material, the second chamber is configured to contain the second material, and the third chamber is configured to contain the third material;

wherein the information storage portion stores a regimen of doses to enable the control electronics to direct quantities of the first, second, and third materials to be emitted upon activation of the inhalation device as the single inhalable composition, and to direct the quantities of the first and second materials to vary with respect to each other to alter the concentration of the first material relative to the second material in the single inhalable composition over the regimen of doses over the regimen and to direct the quantity of the third material to be regulated over time via the chronometer.

30. The inhalation device of claim 29 further comprising an interface, the interface actionable on the control electronics to adjust emission of at least one of the pharmacologically active materials.

31. The inhalation device of claim 29 further comprising a sensor capable of detecting at lest one externally originated event actionable on the device, the sensor capable of generating at least one signal receivable by the control electronics.

32. The inhalation device of claim 29 wherein the information storage portion of the control electronics includes a look-up table specifying quantities of the first and second materials to be emitted upon activation of the inhalation device.

33. The inhalation device of claim 29 wherein the regimen stored in the information storage portion of the control electronics includes a mathematical algorithm controlling quantities of the first and second materials to be ejected with each activation of the inhaler, the quantities vary with each successive activation.

34. The inhalation device of claim 29 wherein the first, second and third aerosol generators are microfluidic drop ejection devices.

35. An inhalation device comprising:

an inhalation chamber;

means for storing a first material separately from a second material;

means for generating aerosolized quantities of first and second materials from first and second chambers and introducing the materials into the inhalation chamber to form a single inhalable composition, wherein the first material and the second material are pharmacologically different from each other; and means for controlling aerosolized generation of the first and second materials over a regimen of doses such that the quantities of the first and second material are variable with respect to each other to alter the concentration of the first material relative to the second material in the single inhalable composition over the regimen of doses.

* * * * *